United States Patent
Berndt et al.

(10) Patent No.: US 9,063,105 B2
(45) Date of Patent: Jun. 23, 2015

(54) METHOD FOR RECOGNIZING SENSOR POISONINGS AND TEST STATION FOR CARRYING OUT THE METHOD

(71) Applicant: Dräger Safety AG & Co. KGaA, Lübeck (DE)

(72) Inventors: Malte Berndt, Lübeck (DE); Dirk Zastrow, Lübeck (DE); Sven Schimmel, Bad Schwartau (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 14/278,499

(22) Filed: May 15, 2014

(65) Prior Publication Data
US 2014/0342459 A1  Nov. 20, 2014

(30) Foreign Application Priority Data

May 16, 2013  (DE) .......................... 10 2013 008 425

(51) Int. Cl.
  *G01N 31/10* (2006.01)
  *G01N 27/16* (2006.01)
  *G01N 33/00* (2006.01)

(52) U.S. Cl.
  CPC ................ *G01N 31/10* (2013.01); *G01N 27/16* (2013.01); *G01N 33/007* (2013.01)

(58) Field of Classification Search
  USPC ........... 73/1.02–1.04, 1.06–1.07, 23.2, 23.31; 204/401; 422/82.01–82.04, 90, 94–98; 436/37, 140–143, 151–152
  See application file for complete search history.

(56) References Cited

U.S. PATENT DOCUMENTS

| | | | | |
|---|---|---|---|---|
| 3,960,495 A | * | 6/1976 | Tantram | 436/141 |
| 4,116,612 A | * | 9/1978 | Melgaard | 431/76 |
| 4,173,886 A | * | 11/1979 | Archbold et al. | 73/31.02 |
| 4,464,653 A | * | 8/1984 | Winner | 340/501 |
| 4,817,414 A | * | 4/1989 | Hagen et al. | 73/23.31 |
| 5,025,653 A | * | 6/1991 | Schuldt | 73/23.2 |

(Continued)

FOREIGN PATENT DOCUMENTS

| | | |
|---|---|---|
| JP | 2006-003 115 A | 1/2006 |
| WO | 2013/019178 A1 | 2/2013 |

OTHER PUBLICATIONS

Use of "Equivalent" Calibration Gas Mixtures Aug. 8, 2001 3 pages downloaded from http://www.brandtinst.com/biosystems/appnotes/Downloads/2.%20Equivalent_Calibration_Gas.pdf.*

(Continued)

*Primary Examiner* — Arlen Soderquist
(74) *Attorney, Agent, or Firm* — McGlew and Tuttle, P.C.

(57) ABSTRACT

A method for recognizing sensor poisonings in portable gas-measuring devices with a test station having a main unit with a control and analysis unit and test modules connected with the main unit for data exchange with an connected device. The test station recognizes device model and/or gas sensor model of the connected device. The main unit has gas inlets for different test gases and there is a first gas feed line for sending test gas to the test modules and a second gas feed line for sending purging gas to the test modules and a gas drain line to return gas from the test modules to the main unit. The method includes detection of a first measured value and of a second measured value and determination of sensor poisoning on the basis of the two values. The test station control and analysis unit carries out the method.

22 Claims, 4 Drawing Sheets

(56) References Cited

U.S. PATENT DOCUMENTS

| | | | |
|---|---|---|---|
| 5,069,879 A * | 12/1991 | Leichnitz et al. | 422/86 |
| 5,214,952 A * | 6/1993 | Leggett et al. | 73/1.03 |
| 5,234,837 A * | 8/1993 | Accorsi et al. | 436/159 |
| 5,513,125 A * | 4/1996 | Kauschke | 702/24 |
| 5,582,797 A * | 12/1996 | Kewley et al. | 422/83 |
| 5,670,115 A | 9/1997 | Cheng et al. | |
| 5,858,739 A * | 1/1999 | Williams | 436/151 |
| 5,948,962 A * | 9/1999 | Matthiessen | 73/23.2 |
| 5,985,673 A * | 11/1999 | Bao et al. | 436/151 |
| 5,993,743 A * | 11/1999 | Nordman et al. | 422/94 |
| 6,053,030 A * | 4/2000 | Whynall et al. | 73/23.2 |
| 6,053,031 A * | 4/2000 | Kullik et al. | 73/31.05 |
| 6,085,576 A * | 7/2000 | Sunshine et al. | 73/29.01 |
| 6,096,560 A * | 8/2000 | Scripca et al. | 436/164 |
| 6,172,759 B1 * | 1/2001 | Goldstein | 356/437 |
| 6,182,497 B1 * | 2/2001 | Krajci | 73/23.2 |
| 6,237,392 B1 * | 5/2001 | Yu et al. | 73/1.06 |
| 6,362,741 B1 * | 3/2002 | Hickox et al. | 340/605 |
| 6,423,962 B1 * | 7/2002 | Pepper | 250/222.1 |
| 6,442,639 B1 * | 8/2002 | McElhattan et al. | 710/303 |
| 6,606,897 B1 * | 8/2003 | Koyano et al. | 73/23.2 |
| 6,632,674 B1 * | 10/2003 | Warburton | 436/8 |
| 6,640,608 B2 * | 11/2003 | Pepper et al. | 73/1.02 |
| 6,679,094 B2 * | 1/2004 | Wang et al. | 73/1.06 |
| 6,918,281 B2 * | 7/2005 | Sussman et al. | 73/1.06 |
| 7,051,577 B2 * | 5/2006 | Komninos | 73/40.5 A |
| 7,089,778 B2 * | 8/2006 | Rabenecker et al. | 73/23.2 |
| 7,257,986 B2 * | 8/2007 | Haupt et al. | 73/23.2 |
| 7,377,147 B1 * | 5/2008 | Scheffler et al. | 73/1.06 |
| 7,530,255 B2 | 5/2009 | Frank et al. | |
| 7,588,726 B1 * | 9/2009 | Mouradian et al. | 422/83 |
| 7,655,186 B2 * | 2/2010 | Tobias | 422/83 |
| 7,661,290 B2 * | 2/2010 | Gu et al. | 73/1.03 |
| 7,840,366 B1 * | 11/2010 | Moses et al. | 702/85 |
| 7,937,984 B2 * | 5/2011 | Tobias | 73/1.06 |
| 7,975,524 B2 * | 7/2011 | Sakai et al. | 73/1.06 |
| 8,163,242 B2 * | 4/2012 | Elkins | 422/83 |
| 8,342,002 B2 * | 1/2013 | Shindo et al. | 73/1.06 |
| 8,409,504 B2 * | 4/2013 | Bossoutrot et al. | 422/54 |
| 8,537,020 B2 * | 9/2013 | Thorson | 340/632 |
| 8,539,809 B2 * | 9/2013 | Hemmingsson et al. | 73/1.06 |
| 2002/0050161 A1 * | 5/2002 | Warburton | 73/23.2 |
| 2002/0140675 A1 * | 10/2002 | Ali et al. | 345/158 |
| 2002/0146352 A1 * | 10/2002 | Wang et al. | 422/96 |
| 2002/0168772 A1 * | 11/2002 | Lloyd et al. | 436/37 |
| 2004/0074279 A1 * | 4/2004 | Forrest | 73/1.06 |
| 2004/0121470 A1 * | 6/2004 | Fung et al. | 436/37 |
| 2004/0145485 A1 * | 7/2004 | Tice | 340/632 |
| 2005/0000981 A1 * | 1/2005 | Peng et al. | 222/3 |
| 2005/0092063 A1 * | 5/2005 | Tajima et al. | 73/23.2 |
| 2005/0155405 A1 * | 7/2005 | Sasaki et al. | 73/1.06 |
| 2006/0010974 A1 * | 1/2006 | Koyano et al. | 73/431 |
| 2006/0019402 A1 | 1/2006 | Wang et al. | |
| 2006/0042353 A1 * | 3/2006 | Marquis et al. | 73/23.2 |
| 2006/0081033 A1 * | 4/2006 | Peng | 73/31.05 |
| 2006/0101925 A1 * | 5/2006 | Peng et al. | 73/864.41 |
| 2006/0144123 A1 * | 7/2006 | Sunshine | 73/23.2 |
| 2006/0165561 A1 * | 7/2006 | Rohrbacker | 422/68.1 |
| 2006/0263254 A1 * | 11/2006 | Lee | 422/83 |
| 2007/0182573 A1 * | 8/2007 | Lin et al. | 340/632 |
| 2007/0186618 A1 * | 8/2007 | Ackerman | 73/1.06 |
| 2008/0257732 A1 | 10/2008 | Nakano et al. | |
| 2009/0056408 A1 * | 3/2009 | Tryfonos et al. | 73/1.06 |
| 2010/0212395 A1 * | 8/2010 | Willett et al. | 73/1.06 |

OTHER PUBLICATIONS

TIM® Total Instrument Manager Instruction Manual Software Rev. 2.0 Copyright 2002, 87 pages, downloaded from http://site.msagasmonitors.com/MSA/pdf/TIM-total-instrument-manager_manual.pdf.*

Applications Note: Use of "pentane equivalent" calibration gas mixtures Jul. 10, 2003, 5 pages downloaded from http://www.conceptcontrols.com/pdf/Use-of-pentane-equivalent-calibration-gas-mixtures.pdf.*

MicroDock II Automated Instrument Docking Station copyright 2007, 2 pages downloaded from http://www.apc.co.nz/site/associatedprocess/images//items/associatedprocess_01214.pdf.*

Microdock II User Manual copyright 2008 93 pages downloaded from http://www.enviromed.ca/Instruments/Manuals/MicroDock-II_UserManual.pdf.*

Matheson Portables TM catalog copyright 2012, 38 pages downloaded from http://www.mathesongas.com/pdfs/litCenter/SpecGas&EquipmentBrochures/Portable%20Cylinders%20Catalog.pdf.*

* cited by examiner

METHOD FOR RECOGNIZING SENSOR POISONINGS AND TEST STATION FOR CARRYING OUT THE METHOD

CROSS REFERENCE TO RELATED APPLICATIONS

This application claims the benefit of priority under 35 U.S.C. §119 of German Patent Application DE 10 2013 008 425.3 filed May 16, 2013, the entire contents of which are incorporated herein by reference.

FIELD OF THE INVENTION

The present invention pertains to a method for recognizing sensor poisonings in portable gas-measuring devices by means of a test station as well as to a test station for carrying out this method.

BACKGROUND OF THE INVENTION

Portable gas-measuring devices are usually used by persons who are located in areas in which they may be exposed to harmful gases. Such gas-measuring devices may be equipped with different models of sensors, e.g., infrared sensors, semiconductor sensors, electrochemical sensors, catalytic sensors or the like. However, the phenomenon of the so-called sensor poisoning plays a major role in respect to the ability of the gas sensor and hence of the gas-measuring device to function especially in the case of catalytic sensors.

Such catalytic sensors typically recognize not only a special gas, but there are so-called cross sensitivities, i.e., the sensor recognizes a plurality of different gases simultaneously, without being able to concretely indicate which of these gases it is actually measuring. However, the sensitivity to these gases may be different. The sensitivity to the recognized gases decreases in the course of the aging of such sensors. However, the sensitivity does not decrease uniformly for all recognized gases. The process is rather affected by the concrete history of the individual gas sensor, i.e., by the ambient and storage conditions and the gas species and quantities of gases to which the sensor was already exposed in the course of its life. However, the sensor may be damaged or poisoned above all by certain substances. Among others, substances such as silicon, sulfur compounds and polymerizing substances lead to such a poisoning in case of catalytic EX sensors (sensors that are used in an environment with potential explosion hazard and/or can detect explosible/explosive gases). One speaks of sensor poisoning in this connection if a certain gas or vapor to be detected cannot be processed in the catalytic sensor any longer and thus it cannot be detected any longer, or when the sensitivity is insufficiently low to initiate the necessary actions, e.g., alarms. The sensor in this case indicates a measurement result that is much too low compared to the actually present concentration of the gas to be detected. It may in this case happen that a sensor, which can measure a plurality of different gases, continues to correctly indicate a first gas, but it does not any longer correctly measure a second gas, for which it is already poisoned. This is especially significant if the calibrating gas, i.e., the gas with which the sensor sensitivity is set, corresponds to the gas for which the normal sensitivity was maintained. The loss of sensitivity for the second gas can thus remain suppressed.

Such a sensor poisoning may become especially relevant, for example, in case of catalytic sensors that shall detect combustible gases, e.g., in the area of firefighting, but also in the petrochemical industry, chemical industry or in mining.

Such catalytic sensors can also recognize, besides methane, for example, different other gases and vapors, e.g., propane, pentane, butane or nonane and toluene or the like. For example, sensors that are used in the area of firefighting and shall indicate the presence of combustible gases or vapors, are often set by means of toluene or nonane, because they have a comparatively low sensitivity to these vapors. It is in this case assumed that a sensor thus set will adequately detect the entire range of combustible gases and vapors. However, it may be problematic that the sensitivity of the sensor to toluene and nonane is often retained for a long time, while the sensitivity to, e.g., methane declines much sooner, which is also called selective sensor poisoning for methane (or another corresponding gas). The gas sensor in this case measures the quantity of all gases present as a so-called sum signal, i.e., as a sum of a plurality of signals. The sum is composed of the individual measured values of the gases present. It cannot be recognized on the basis of the sum how high the actual percentage of the particular gases measured is. At the same time, the gas sensor is typically also unable to resolve the sum signal into the individual components. Thus, there may be a risk that the actually present concentrations of individual combustible gases, especially methane, but also of another gas, for which the sensor is already poisoned, is estimated incorrectly at an operating site. This may lead to drastic consequences for the user of the gas-measuring device in the worst case.

For example, US 2008/0257732 A1, US 2006/0019402 A1, and U.S. Pat. No. 5,670,115 A describe in this connection that sensor poisonings are determined by means of various calibrating or test gases, and the gas sensor to be tested is exposed to the calibrating or test gases one after another.

Test stations for gas-measuring devices, in which different test gases can be admitted simultaneously to a plurality of gas-measuring devices, are known from the documents JP 2006-003 115 A, U.S. Pat. No. 7,530,255 B2, and WO 2013/019178 A1.

SUMMARY OF THE INVENTION

Based on this, an object of the invention is to provide a method and a test station for carrying out the method, with which method the risk of incorrect estimation of a present concentration of a gas can be reduced.

In a method for recognizing sensor poisonings in portable gas-measuring devices by means of a test station, wherein the test station has a main unit including a control and analysis unit and wherein the test station has a plurality of test modules, which are connected with the main unit for data exchange, and into which a gas-measuring device each can be inserted (connected), wherein the test station has means for recognizing the model of the device for detecting the model of the device and/or the model of the gas sensor of the particular gas-measuring device inserted into a test module, wherein the main unit has a plurality of gas inlets for different test gases and wherein the test station has a first gas feed line, through which test gas can be sent to the test modules, a second gas feed line, through which a purging gas can be sent to the test modules, and a gas drain line, through which gas can be sent from the test modules back to the main unit, the present invention makes provisions for the method to have the following steps:

a. Insertion of at least one gas-measuring device into at least one of the test modules of the test station;
b. Recognition of the model of the gas sensor of the gas-measuring device inserted and/or of the model of the gas-measuring device inserted by the means for recognizing the device model of the test station;

c. Transmission of the recognized gas sensor model and/or of the model of the device of the gas-measuring device inserted at the control and analysis unit;

d. Selection of a first test gas suitable for the model of the gas sensor of the gas-measuring device inserted by the control and analysis unit;

e. Connection of the gas inlet, through which the selected test gas can be fed, to the first gas feed line in the test station;

f. Feeding of the first test gas to the test module, in which the gas-measuring device is inserted;

g. Detection of a first measured value by the gas sensor;

h. Optionally: Purging of the gas-measuring device and of the gas sensor by means of a purging gas, which is sent through the second gas feed line from the main unit to the test module, in which the gas-measuring device is inserted;

i. Selection of a second test gas suitable for the model of the gas sensor of the gas-measuring device inserted by the control and analysis unit;

j. Connection of the gas inlet, through which the selected second test gas can be fed, to the first gas feed line in the test station;

k. Feeding of the second test gas to the test module, in which the gas-measuring device is inserted;

l. Detection of a second measured value by the gas sensor; and m. Determination whether a sensor poisoning is present on the basis of the first measured value detected and the second measured value detected.

A first gas feed line, through which test gas can be sent to the test modules, will also be called test gas feed line (test gas line) below. The second gas feed line, through which purging gas can be sent to the test modules, will also be called purging gas line (purging gas feed line).

Whether a sensor poisoning possibly occurs can be determined rapidly and in a simple manner based on the first and second measured values by means of the test station with such a method. For example, information on the measured value, that is ideally expected (expected measured value) for the particular model of gas sensor (sensor model) for a certain gas at a preset concentration of the gas in a gas mixture, can be stored for this in the control and analysis unit.

The analysis can then be based on the knowledge of the cross sensitivities of the two gases to one another. For example, the indicated measured value of the two gases is put into relationship with one another. If the value is below a limit, which can be considered to be sufficiently safe from the viewpoint of the protection of persons, it is meaningful to classify the sensor as being poisoned. For example, a value for the lower explosion limit (LEL) of a gas in a gas mixture may be stored for this. It may also be provided that a value that is markedly lower than the lower explosion limit, e.g., 50% of the lower explosion limit (50% LEL), is stored to ensure that the presence of corresponding combustible gases is detected in time in all cases.

Catalytic sensors, which detect a plurality of different such gases due to corresponding cross sensitivities, are typically not uniformly sensitive for all these gases. There are, for example, sensors that indicate, when exposed to a gas that contains methane at a concentration corresponding to 50% LEL, that methane is contained at a concentration of 50% LEL. However, when exposed to propane at a concentration of 50% LEL, the same sensor indicates only that propane is present at a concentration of 29% LEL. Such an exemplary sensor would therefore be expected, when exposed to a corresponding gas, to indicate 50% LEL for methane corresponding to 50% LEL and to indicate 29% LEL for propane. The expected measured value would be correspondingly 50% LEL for methane and 29% LEL for propane. Such values are usually known for the respective models of sensors and can therefore be correspondingly stored in the control and analysis unit.

In a very simple embodiment, it is possible, for example, for catalytic sensors, which are used as a primary measure in the protection against personal injuries due to explosions, to check whether after adjusting to the first, more insensitive gas, the second, more sensitive gas reaches at least the concentration that was fed. Thus, even though the ratio would drop to 1:1, but triggering an alarm in due time would still always be guaranteed.

To recognize selective poisonings in time, it is, however, recommended that a sensor-specific value be determined, which must not be undershot. This value can be determined experimentally. It is consequently advantageous if the test station with which the method is carried out is a test station in which measured values expected in the control and analysis unit are stored for a plurality of gas sensor models and/or for gases that are to be measured. What measured values are stored in the individual gas sensor models depends logically on the particular gas sensor model.

It may also be provided in this connection that information is stored in the control and analysis unit for individual models of gas sensors on which gas mixture can be used as the first test gas, which gas mixture as the second test gas, what measured value is expected in case of exposure to the first test gas and what measured value is expected on exposure to the second test gas. It may also be provided, as an alternative, that information is stored on which gas mixture can be used as the first test gas, which gas mixture can be used as the second test gas and on the ratio of the first measured value that is expected on exposure to the first test gas to the second measured value that is expected on exposure to the second test gas.

To determine whether a gas-measuring device or a gas sensor, which is used in a gas-measuring device, is still sufficiently in good working order to recognize a hazardous situation in time and reliably, the following procedure can then be followed by means of the method according to the present invention.

The gas-measuring device to be tested, i.e., the gas-measuring device in which a gas sensor to be tested is installed, is inserted into a test module corresponding to the steps a. through c. of the method according to the present invention. The test station in this case recognizes the gas-measuring device model that was inserted or what gas sensor model or, if a plurality of gas sensors are installed in the gas-measuring device, the gas sensor models the gas-measuring device inserted contains. The test station can preferably recognize both, i.e., the test station recognizes the model of gas-measuring device that was inserted and the model of gas sensor or the models of gas sensors that are installed in the gas-measuring device. This is advantageously carried out by means of the device model recognition means. Each test module advantageously has such a device model recognition means. The test module then transmits the recognized information via corresponding data exchange means, by which the test module is connected with the main unit for data exchange, to the control and analysis unit of the main unit.

Based, as was described above, on data stored in the control and analysis unit of the main unit, the control and analysis unit of the test station then selects, corresponding to step d. of the method according to the present invention, a first test gas, with which it can be determined, in principle, whether the gas sensor of the gas-measuring device, which said gas sensor is to be tested, is in good working order. A test gas is a gas mixture that contains one or more gases of a known composition. A gas mixture is defined, in principle, as a gas that contains one or more different gases with a known or unknown composition. If it shall be checked, for example, whether a catalytic sensor detects combustible gases correctly, the first test gas may be, for example, a gas mixture that contains combustible gases with a known composition.

The test station with which the method is carried out has a plurality of gas inlets, to which, for example, a pressurized gas cylinder each, which contains a certain test gas, can be connected. This is especially advantageous if the selection of test gases shall be able to be chosen individually. Individual pressurized gas cylinders can be replaced rapidly and simply in this case, as a result of which different test gases can correspondingly be made available, depending on the individual requirements of the operator of the test station. However, it may also be provided that stationary gas feed lines for such test gases are connected to the gas inlets. The control and analysis unit of the main unit of the test station in this case has corresponding information on what test is connected to which gas inlet. This can be recognized either by the control and analysis unit by means of a recognition device, or it is programmed correspondingly in the control and analysis unit by the operator of the test station. Corresponding connection data may, of course, also be preset and stored in the control and analysis unit. After the control and analysis unit of the test station has selected the suitable first test gas, it gives a prompt for the gas inlet through which the selected test gas can be fed to become connected, corresponding to step e. of the method according to the present invention, to become connected with the first gas feed line of the test station. This can take place, for example, by sending a corresponding control command to one or more valves in the test station.

If the corresponding gas port of the main unit is connected with the first gas feed line (connected to the first gas feed line), the test station can send, corresponding to step f. of the method according to the present invention, the first test gas to the test module, into which the gas-measuring device to be tested is inserted. The gas-measuring device will then measure the first test gas fed to it in just the same way as it would measure any other gas mixture during use in a real situation, and it sends a first measured value. Adjustment may optionally also be made to the first measured gas in this step, i.e., the first measured value is corrected such that it corresponds to the concentration in the test gas cylinder. This first measured value is detected by the test module and preferably transmitted by means of the data exchange means to the main unit, namely, to the control and analysis unit of the test station. A first measured value of the gas sensor is thus detected corresponding to step g. of the method according to the present invention. If the gas-measuring device to be tested contains a plurality of gas sensors, it is conceivable that steps d. through g. are carried out separately for each of these gas sensors.

To remove residues of the first test gas from the gas-measuring device to be tested following this first measurement and to thus prevent the subsequent second measurement from being possibly distorted, it may be useful to purge the gas-measuring device with a purging gas in a next step. The method according to the present invention therefore provides for the purging of the gas-measuring device inserted and of the gas sensor as an optional step h. by means of a purging gas, which is sent through the second gas feed line from the test station to the test module, into which the gas-measuring device is inserted. A purging gas is typically a neutral (inert) gas, in which the gas sensor does not detect any gases that are to be detected. This may be, for example, normal air. Depending on the environment in which the test station is used, this air may be fed through a pressurized cylinder, or it may also be taken up from the ambient air, for example, by means of a pump. The test station advantageously has a gas port for this in its main unit, which port can be connected either with a corresponding purging gas cylinder or with the ambient air. This gas port is preferably connected with the second gas feed line of the test station. The purging gas can be sent through this second gas feed line to the test modules, and the control and analysis unit of the test station can transmit the command for switching over from the first gas feed line to the second gas feed line to the test modules. The transmission preferably takes place via data exchange means. It may also be provided, as an alternative, that each test module has a control unit (test module control unit) of its own. This test module control unit can then control a switchover from the first gas feed line to the second gas feed line, which switchover is independent from the main unit.

Regardless of whether step h. is performed after detection of the first measured value or not, a second measured value is detected corresponding to the method according to the present invention by carrying out steps i. through l., in order to be finally able to determine, in step m., whether a sensor poisoning is possibly present. Steps i. through l. are carried out as was already described above for steps d. through g., step i. being carried out analogously to step d, step j. analogously to step e., step k. analogously to step f., and step l. analogously to step g. It is recognized that it is also readily possible in an alternative order in which the method is carried out to carry out step i. (selection of a second test gas suitable for the model of the gas sensor) already immediately after step d. and hence before step e.

To determine, corresponding to step m., whether sensor poisoning is present, the first measured value, which was detected in step g., and the second measured value, which was detected in step l., are compared with the respective expected measured values. The comparison may be carried out automatically by the control and analysis unit. However, it may also be provided that the control and analysis unit only passes on the actual measured values and the corresponding expected measured values to an output unit and an operator of the test station decides on the basis of this information whether or not sensor poisoning is present. It may also be provided, for example, that the operator receives the expected and actual measured values displayed on a display device (display), that the expected and actual measured values are outputted via a printing device, or even that these are transmitted to another terminal, e.g., a computer of the operator, and are analyzed there by the operator. However, the control and analysis unit preferably performs the comparison automatically and outputs only the result, namely, the determination of whether or not sensor poisoning is possibly present. It is even conceivable, in an especially preferred manner, that the control and analysis unit outputs the result in the form of a control command, which it selects on the basis of the result. Various scenarios are conceivable, e.g., the following: If the control and analysis unit arrives at the result that a sensor poisoning is possibly present, this control command may be, for example, that the corresponding gas-measuring device is blocked from further use. It may also be provided that the control command is the sending of a warning signal, the blocking of the removal of the gas-measuring device from the test module or something similar.

In any case, the result is determined by comparison of the first measured value with the second measured value. For example, the ratio of the first measured value to the second measured value can be formed. If the two measured values essentially correspond to the expected measured values or they deviate from the expected measured values by a constant error, which is generated by an incorrect setting of the sensor only, the ratio of the two measured values corresponds to the ratio of the expected measured values. If, however, there is sensor poisoning, the error with which the first measured value deviates from the expected first measured value from the error with which the second measured value deviates from the expected second measured value. As a consequence, the ratio of the first measured value to the second measured value also deviates significantly from the ratio of the expected first measured value to the expected second measured value. The limits within which a deviation of the ratio of the real measured values from the ratio of the expected measured values are considered to be a significant deviation may be stored preferably for each gas-measuring device to be tested or for each model of gas sensor to be tested in the control and analysis unit. It may also be provided that these limits are set and programmed by the operator when the test station is put into operation or during the operation of the test station.

It may also be provided that in case of a non-automatic analysis, in which the values are only displayed, for example, to the operator, the measured values or the ratios of the measured values are checked only by the operator comparing them, for example, with values present in tables or in another form or by a similar procedure. As an alternative to the comparison of the measured value ratios formed as described above, it may also be provided in such a case that a direct comparison of the measured values with the expected values is performed. For example, the operator can determine in this case for each measured value how great the error is by which the real measured value deviates from the expected measured value and then compare the errors with one another. If the two measured values deviate from the expected values by an equal error or an error that is similar within narrow limits, sensor poisoning is very likely to be absent and there is only an incorrect adjustment of the sensor by this more or less constant error. However, if the errors deviate markedly from one another, there is a possibility that a sensor poisoning is present. It is obvious that this procedure can also be carried out automatically by the control and analysis unit of the test station.

It is thus favorable in any case if the determination of whether a sensor poisoning is present in step m. comprises the following steps:

m.1 Transmission of the first measured value and of the second measured value to the control and analysis unit of the test station;
m.2 Determination of the ratio of the first measured value to the second measured value; and
m.3 Outputting of the ratio by means of an output unit and/or selection of a follow-up action by the control and analysis unit of the test station on the basis of the ratio determined.

Step m.2 may also be, as an alternative, a determination of the ratio of the errors by which the real first measured value, i.e., the first measured value detected in step g., deviates from the expected first measured value and by which the real second measured value, i.e., the second measured value detected in step l., deviates from the expected second measured value, as was explained above.

If only the ratio is outputted in step m.3 without a further follow-up action being selected by the test station, the operator can select an individual subsequent reaction on the basis of this outputted information.

The selection of a follow-up action by the control and analysis unit is advantageously performed by a comparison of the ratio determined in step m.3 with a ratio being stored in the control and analysis unit. The control and analysis unit in this case determines by how much the determined ratio deviates from the stored ratio and selects a follow-up action in the form of a control command on the basis of the result obtained in this case for the deviation. If no ratios are being stored in the control and analysis unit, but only individual expected measured values, the control and analysis unit may also form first the ratio of the expected measured value for selecting the follow-up action and subsequently compare this ratio with the ratio of the real measured values detected in steps g. and l.

It is recognized that it is always advantageous if the first test gas contains a gas that is to be measured during the operation of the gas-measuring device at a first, known concentration and if the second test gas contains the gas to be measured at a second, known concentration, which is different from the concentration of the gas in the first test gas. It may also be advantageous in this case if the second test gas contains, in addition to the gas to be measured, at least one gas for which the gas sensor model present in the gas-measuring device inserted has cross sensitivity. It is especially favorable in this connection, if the gas for which there is cross sensitivity is not a component of the first test gas. The first and/or second test gas may be selected especially preferably from the group containing propane, propane mixed with $H_2S$, $CO$, $O_2$ and/or $CO_2$, pentane, pentane mixed with $H_2S$, $CO$, $O_2$ and/or $CO_2$, butane, hydrogen as well as mixtures of these gases and gas mixtures mentioned. Further gaseous or vapor components may also be added, e.g., toluene, nonane, methane, propane, butane, hydrogen, pentane or even mixtures thereof.

In a method according to the present invention, in which the test station is advantageously designed such that each test module has a gas feed line, which can be connected with a gas inlet of the gas-measuring device to be tested, which said line has a first feed valve and a second feed valve and which can be connected with the first gas feed line via the first feed valve and with the second gas feed line via the second feed valve, the present invention preferably makes, in addition, provisions for the feeding of the first test gas to the test module in step f. and for the feeding of the second test gas to the test module in step k. to contain the following respective steps:

| | |
|---|---|
| f.1 and k.1 | Closing of the second feed valve; |
| f.2 and k.2 | Opening of the first feed valve. |

As was already described above, the first gas feed line is the test gas feed line and the second gas feed line is the purging gas feed line here as well. The gas inlet of the gas-measuring device to be tested is the gas inlet via which the gas-measuring device draws in the gas to be measured during intended use.

It may also be provided in any case that a plurality of gas-measuring devices can be inserted simultaneously into the test station. The gas-measuring devices may also be inserted at different times into the test station. The respective test module, in which a gas-measuring device is inserted at any desired time, then transmits, independently from the other test modules of the test station, the information to the main unit that a gas-measuring device was inserted and which gas sensor model or which gas sensor models and/or which device model was recognized. The control and analysis unit can then select the corresponding first test gas, likewise independently from the state of the other test modules.

Furthermore, steps h. and i. as well as m. of the method according to the present invention can be carried out for each test module, into which a gas-measuring device was inserted, independently from the state of the remaining test modules. In other words, the control and analysis unit can determine, for example, for a certain test gas, which can be fed via one of the gas inlets to the first gas feed line of the test station, for which test modules this test gas is needed either as a first test gas or as a second test gas.

By contrast, steps e. through g. and steps j. through l. are preferably carried out synchronously for all test modules of the test station. Steps e. and j. and steps f. and k. as well as steps g. and i. can be carried out simultaneously for different test modules that are fundamentally different from one another. However, it is useful if each test module performs all steps a. through m. at least once for each gas-measuring device that is inserted into the test module.

The following would be, for example, a conceivable course of such a method: By performing steps a. through d. or by performing step i. for all test modules independent from one another, the control and analysis unit determines, as was described above, which test gas the individual test modules need in the respective next step, i.e., step e. or step j. The control and analysis unit then determines which of these needed test gases shall be sent as the next gas through the first gas feed line of the test station. The feed of the test gas from the first gas feed line is then interrupted, preferably for all test modules that do not need this test gas, by closing the feed valve that is arranged between the test gas feed line and the respective test module. As a consequence, only the test modules that need the same test gas in the next step are connected with the first gas feed line fluidically. Corresponding to steps e. and j., respectively, the gas inlet, through which the selected test gas can be fed, is then connected as the next step to the first gas feed line in the test station and the test gas is sent to the test modules as described above corresponding to steps f. and k., respectively. Finally, a measured value is determined according to steps g. and l., respectively, for each test module, consequently for each gas-measuring device to which the test gas was admitted in the preceding step. It is then determined again for all test modules, independently from one another, whether the gas-measuring device in question has already run through all steps a. through l. and whether it is thus possible to carry out step m. for the test module in question or the gas-measuring device inserted. It is possible to perform step m. when both a first measured value and a second measured value were detected for the test module in question or the gas-measuring device inserted into the test module in question. Step m. is carried out for the test modules for which it is possible to carry out this step. The corresponding, still missing measured value is detected corresponding to the above-described method for the test modules for which it is not possible to carry out step m.

It is consequently recognized that in case a plurality of gas-measuring devices are or will be inserted into the test station, it is advantageous if the method has the following steps:

A Carrying out of steps a. through d. and/or carrying out of step i. for each of the gas-measuring devices independently from one another;

B Determination by means of the control and analysis unit which of the test modules are equipped with gas-measuring devices and which of these gas-measuring devices need the same test gas as the next test gas;

C Closing of the feed valve that is arranged between the test gas feed line and the respective test module for all test modules that do not need the test gas selected in B in the next step; and D Carrying out steps e. through h. or steps j. through m. for each of the gas-measuring devices determined in B independently from one another;

wherein each of the steps a. through m. is carried out at least once for each gas-measuring device that is inserted into a test module of the test station. However, it is also useful if steps a. through m. are carried out for each test module into which a gas-measuring device is inserted in the above-described order from a. to m. However, it may also be provided that the steps are carried out in the order a., b., c., d. i., e., f., g., h., j., k., l., m. or in the order a., b., c., d., i., j., k., l., h., e., f., g., m., and step h. is an optional step, which may be carried out in any case, as before, at any other desired point and/or at a plurality of points of the method.

On the whole, the course of the method for a gas-measuring device that is inserted into a test module when other gas-measuring devices are already present in the test station for testing is in this case, for example, as follows:

Insertion of the gas-measuring device into one of the test modules corresponding to step a. The gas-measuring device is preferably inserted when the feed valve that is arranged between the first feed line and the respective test module is closed, Recognition of the model of the device and/or of the gas sensor corresponding to step b., Transmission of the recognized model of the device and/or of the model of the gas sensor corresponding to step c., Selection of the first test gas by the control and analysis unit corresponding to step d. and/or selection of the second test gas by the control and analysis unit corresponding to step i., Waiting until one of the two test gases selected previously is the test gas that shall be sent next through the first gas feed line, Connection of the gas inlet, through which the selected test gas can be fed, to the first gas feed line in the test station, feeding of the test gas to the test module and detection of a first measured value, Determination that step m. cannot yet be carried out because two measured values have not yet been determined, Selection of the second test gas unless this was done already before, Waiting until the second of the two test gases selected previously is the test gas that shall be sent as the next gas through the first gas feed line, Connection of the gas inlet through which the selected test gas can be fed to the first gas feed line in the test station, feeding of the test gas to the test module and detection of a first measured value, and Determination that step m. can be carried out and carrying out of step m.

Further variants of this course are, of course, conceivable as well. For example, it is conceivable that a gas-measuring device is inserted into a test module, which contains a plurality of gas sensors, for which the above-described method is carried out independently from one another. It is advantageous, for example, in this case if both the model of the device and the model or models of the gas sensor/gas sensors of the device are recognized in step b. of the method.

Moreover, it is conceivable that so-called filter breakthroughs can be detected by means of the method according to the present invention. For example, filters that are selectively permeable for certain gases only can be used if a sensor arranged downstream of the filter shall not measure corresponding gases for which the filter is not permeable. This may be especially useful if the sensor has a cross sensitivity, namely, for a first gas, which shall be detected with the sensor, on the one hand, and, on the other hand, for a second gas, which can be captured (blocked/filtered) by means of the filter and which shall not be detected with the sensor. If, however, the filter is no longer in good working order and becomes permeable for the second gas, which is actually to be captured, one speaks of a filter breakthrough. The second gas, which is in this case flowing unrecognized through the filter, can distort the measured value that is outputted by the sensor. However, such a filter breakthrough is also recognizable by means of the method according to the present invention if the first test gas and the second test gas are selected correspondingly.

In a test station for carrying out the above-described method according to the present invention, the present invention makes provisions for the test station to have a main unit including a control and analysis unit, wherein the test station has a plurality of test modules, which are connected with the main unit for data exchange and into which a gas-measuring device each can be inserted, and the test station has means for recognizing the model of the device in order to detect the model of the device and/or the model of the gas sensor of the respective gas-measuring device inserted into a test module, and the main unit has a plurality of gas inlets for different test gases, and the test station has a first gas feed line, through which test gas can be sent to the test modules, a second gas feed line, through which a purging gas can be sent to the test modules, and a gas drain line, through which gas can be sent back from the test modules to the main unit, and the control and analysis unit is set up to carry out and/or control steps d. through m. of the above-described method according to the present invention.

It is advantageous in this case if the control and analysis unit is set up to carry out and/or control steps B and C corresponding to the above-described method. Furthermore, it is advantageous if the gas feed line of each test module can be connected fluidically with the gas inlet of a gas-measuring device to be tested when the gas-measuring device is inserted into the test module. It is also useful if each test module has a gas drain line, which can be connected with the gas drain line of the test station. The gas feed line of at least one test module preferably has a first feed valve and a second feed valve, and this gas feed line can be connected with the first gas feed line via the first feed valve and with the second gas feed line via the second feed valve.

Further features, details and advantages of the present invention appear from the text of the claims as well as from the following description of exemplary embodiments and from the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
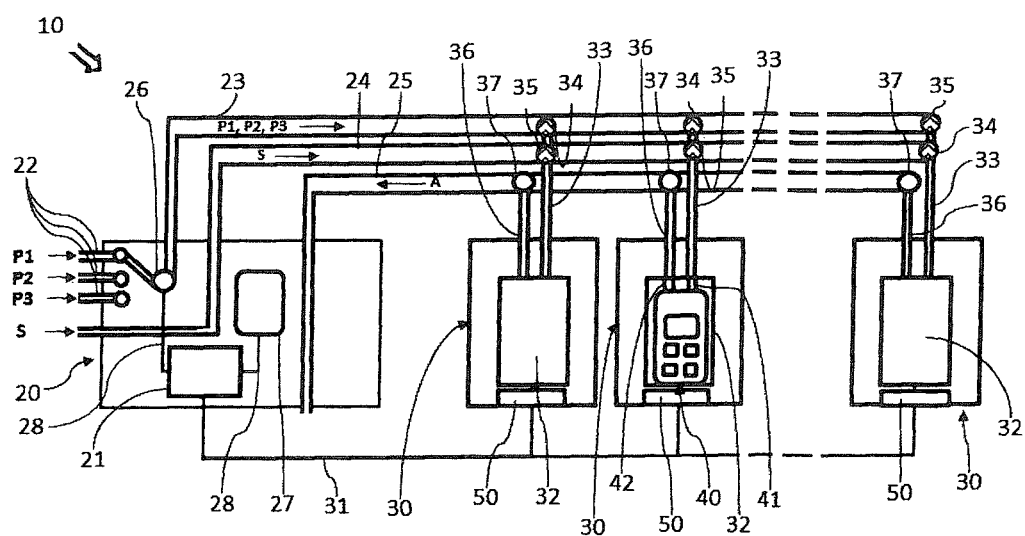
FIG. 1 is a schematic view of a test station for carrying out the method according to the present invention.

Referring to the drawings in particular, a test station 10, which has a main unit 20 and a plurality of test modules 30, is recognized in FIG. 1. The number of test modules 30 is variable. A control and analysis unit 21 is arranged in the main unit 20. The control and analysis unit 21 is connected with an output unit 27 and with a port 26 via data exchange means 28. The output unit 27 is likewise arranged in the main unit 20. However, according to an alternative embodiment, the output unit 27 is a component separate from the main unit 20. The port 26 can be connected with a plurality of gas inlets 22 arranged in the main unit 20. A test gas P1, P2, P3 can flow through each of the gas inlets 22, and a separate gas inlet 22 is preferably provided for each test gas P1, P2, P3. The number of gas inlets 22 is variable, and the three gas inlets 22 shown in FIG. 1 are merely exemplary. More or fewer gas inlets 22 may also be present in alternative embodiments.

Port 26 is connected with a first gas feed line 23, through which the test gas P1, P2, P3 can flow from the main unit 20 to the test modules 30.

A furthermore, a port for a purging gas S, which is connected with a second gas feed line 24 and through which purging gas S can flow to the test modules 30, is formed in the main unit 20. In addition, an outlet is formed in the main unit 20 for gas A flowing back from the test modules 30, which outlet is connected with a gas drain line 25, through which gas A can flow back from the test modules 30 to the main unit 20.

The test modules 30 have a mount 32 each for a gas-measuring device 40. A gas-measuring device 40 typically has a gas inlet 41 and a gas outlet 42. Furthermore, each of the test modules 30 has a device model recognition means 50. Furthermore, the test modules 30 are each connected with the main unit 20, especially with the control and analysis unit 21, via data exchange means 31.

It is recognized that the test modules 30 have a gas feed line 33 and a gas drain line 36 each. The gas feed line 33 is connected with the mount 32 such that the gas feed line 33 can be connected fluidically with the gas inlet 41 of a gas-measuring device 40 inserted into the mount 32. The gas drain line 36 is connected with the mount 32 such that the gas drain line 36 can be connected fluidically with the gas outlet 42 of a gas-measuring device 40 inserted into the mount 32.

The gas feed line 33 has a first feed valve 34. The first feed valve 34 can be connected with the first gas feed line 23. The gas feed line 33 has, in addition, a second feed valve 35. The second feed valve 35 can be connected with the second gas feed line 24. The open or closed state of the first feed valve 34 and the second feed valve 35 are controlled via the control and analysis unit 21 via connections from valve actuators to the control and analysis unit 21. The gas drain line 36 can be connected with the gas drain line 25 via a port 37.

Figure 2A:
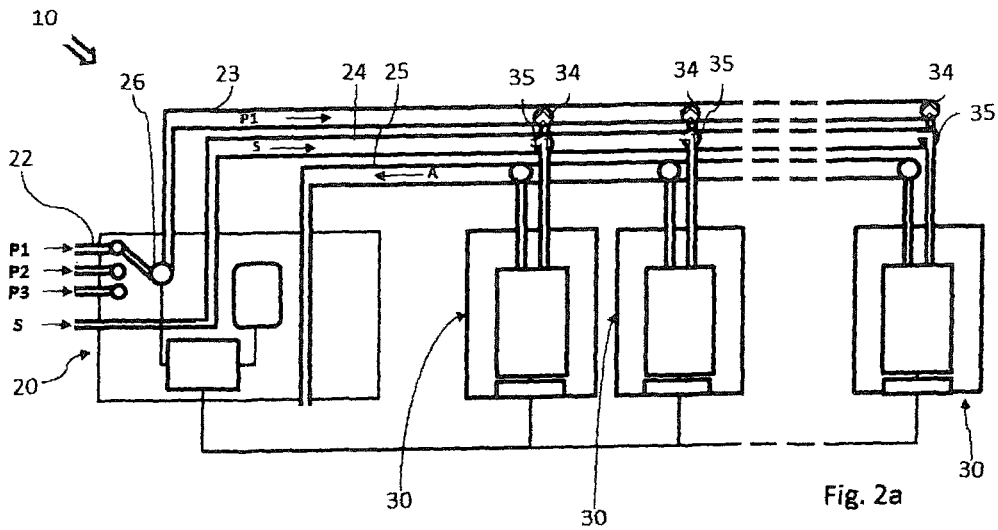
FIG. 2a is a schematic view showing a state during the course of the method for a gas-measuring device inserted into the test station.

A test station 10 can be recognized in FIG. 2a before a gas-measuring device to be tested was inserted into one of the test modules 30. The first feed valves 34 connected with the first gas feed line 23 are closed. The feed valves 35 connected with the second gas feed line 24 are opened. Purging gas S can thus flow through the test modules 30. The port 26 is in a random port position; it is connected here with the gas inlet 22, through which the test gas P1 can be fed.

Figure 2B:
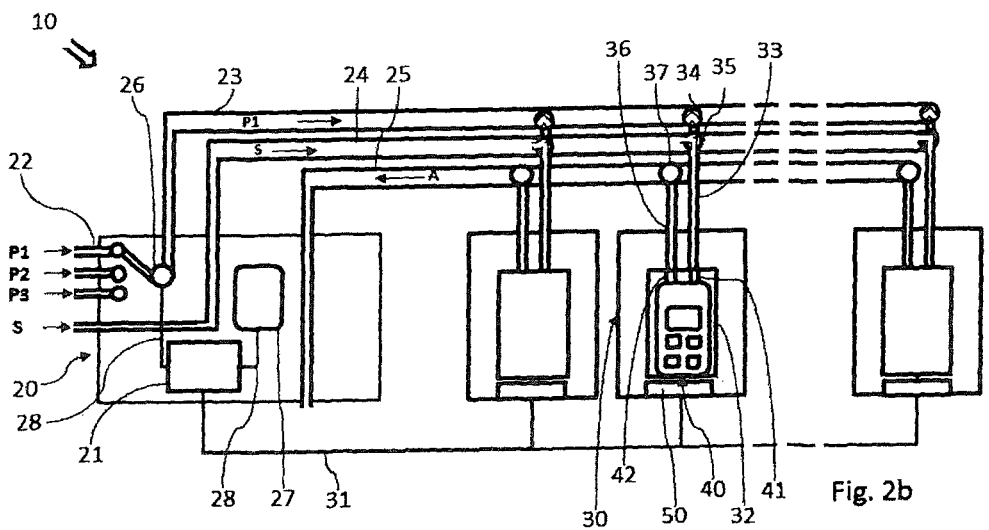
FIG. 2b is a schematic view showing another state during the course of the method for a gas-measuring device inserted into the test station.

Corresponding to step a., a gas-measuring device 40 is inserted in FIG. 2b into one of the test modules 30. The gas inlet 41 of the gas-measuring device 40 is connected with the gas feed line 33, and the gas outlet 42 is connected with the gas drain line 36. According to step b., the device model recognition means 50 recognizes the device model of the gas-measuring device 40, and it optionally even recognizes the gas sensor that is installed in the gas-measuring device 40. The device model recognition means 50 transmits, corresponding to step c., the recognized information, i.e., the recognized model of the gas sensor and/or the recognized device model, to the control and analysis unit 21. This is carried out by means of the data exchange means 31. The first feed valve 34 continues to be closed during these steps a. through c., while the second feed valve 35 is opened, so that purging gas S flows through the gas feed line 33 into the test module 30 and consequently into the gas-measuring device 40 and back again into the gas drain line 25 through the gas outlet 42 and the gas drain line 36.

Figure 2C:
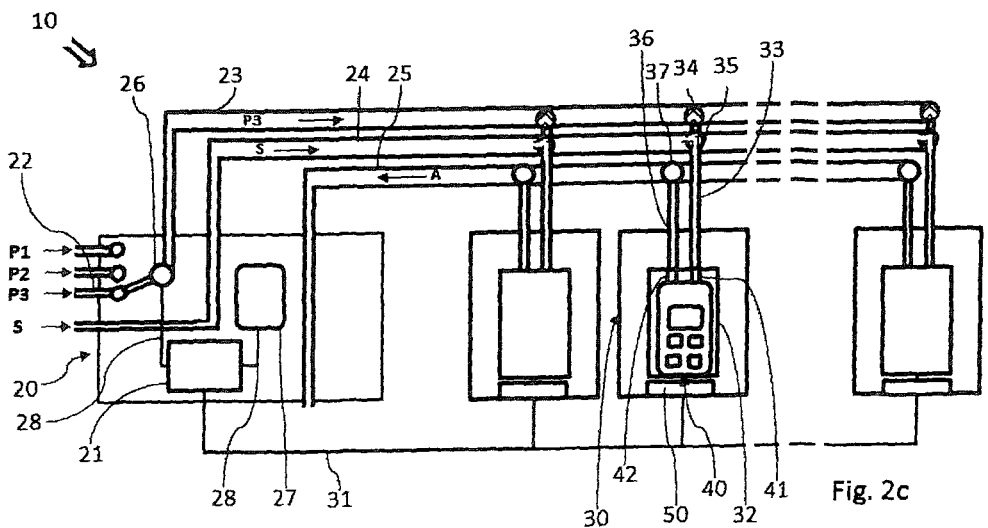
FIG. 2c is a schematic view showing another state during the course of the method for a gas-measuring device inserted into the test station.

After receiving the information transmitted in step c., the control and analysis unit 21 selects, according to step d., a first test gas, which is suitable for the model of the gas sensor of the gas-measuring device 40 inserted, in this case the test gas P3, and connects the gas inlet 22 through which the selected test gas P3 can be fed to the first gas feed line 23 corresponding to step e., as can be recognized in FIG. 2c. It is recognized in FIG. 2c that the test gas P3 will then flow through the first gas feed line 23.

Figure 2D:
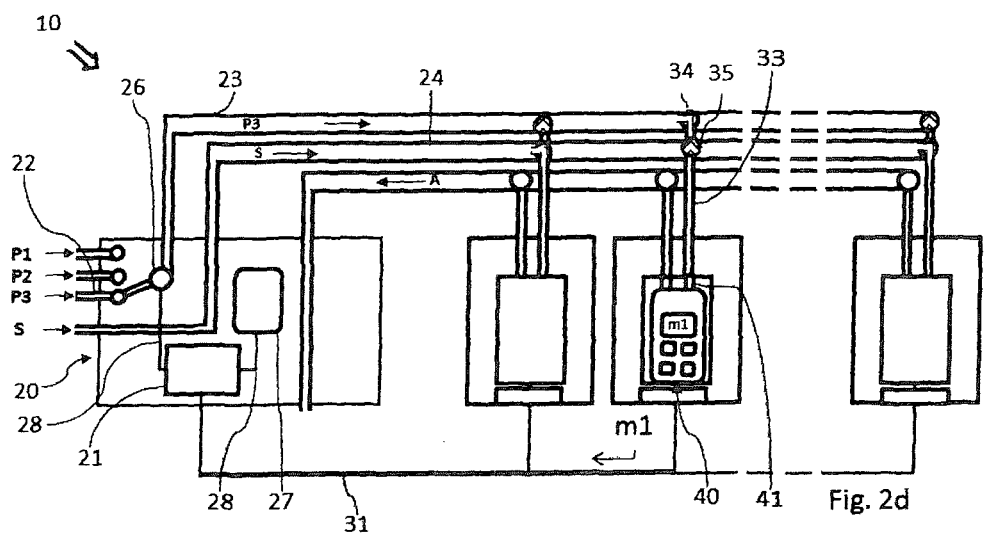
FIG. 2d is a schematic view showing another state during the course of the method for a gas-measuring device inserted into the test station.

According to step f., the test gas P3 is then sent to the test module 30, in which the gas-measuring device 40 is inserted. As can be recognized in FIG. 2d, the second feed valve 35 is closed and the first feed valve 34 is closed for this. The selected test gas P3 can thus flow in this case into the test module 30 and further into the gas-measuring device 40. The gas-measuring device 40 then outputs a first measured value m1, which is passed on to the control and analysis unit 21 via the data exchange means 31. A first measured value m1 of the gas sensor of the gas-measuring device 40 is thus detected according to step g.

Figure 2E:
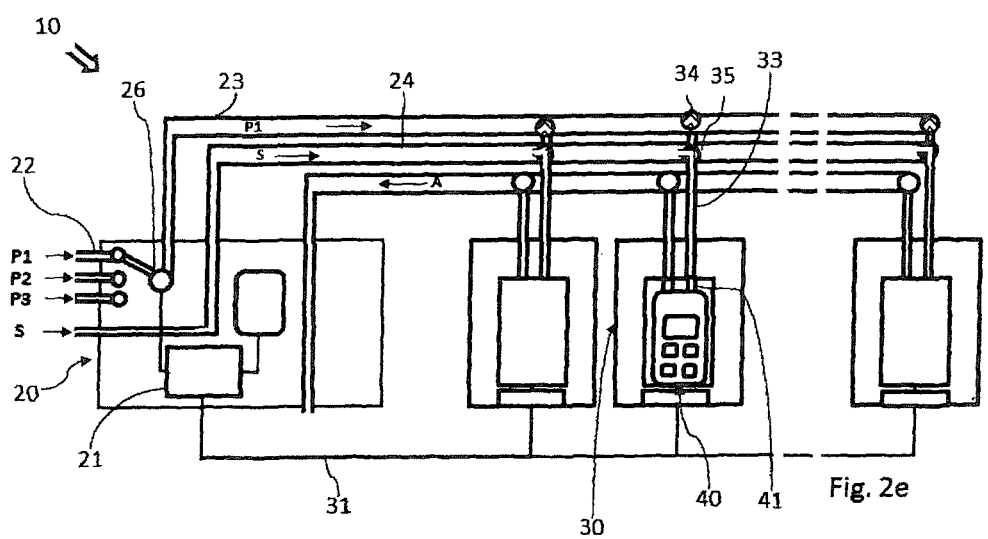
FIG. 2e is a schematic view showing another state during the course of the method for a gas-measuring device inserted into the test station.

After detection of the first measured value m1, it is recognized in FIG. 2e that the gas-measuring device 40 is purged corresponding to step h. The first feed valve 34 is closed and the second feed valve 35 is opened for this. At the same time, the control and analysis unit 21 has already selected, according to step i., a second test gas P1, P2, P3, here the test gas P1, which is suitable for the model of the gas sensor of the gas-measuring device 40 inserted. Furthermore, the control and analysis unit 21 shown in FIG. 2e has already transmitted the control command to the port 26 and has connected the first gas feed line 23 with the gas inlet 22, through which the selected second test gas P1 can be fed. The gas inlet 22, through which the test gas P1 can be fed, is already connected to the first gas feed line 23 according to step j.

Figure 2F:
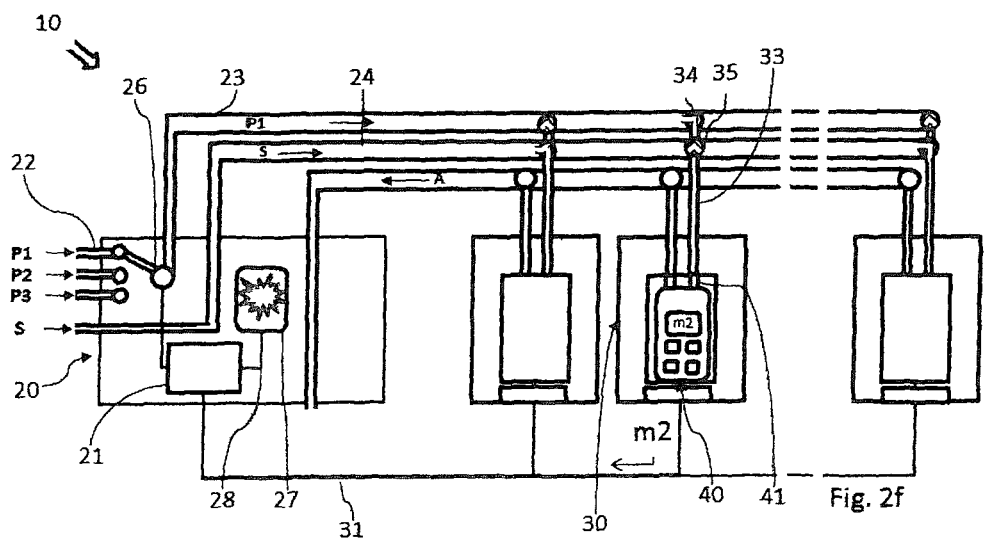
FIG. 2f is a schematic view showing another state during the course of the method for a gas-measuring device inserted into the test station.

According to step k., the test gas P1 is then sent to the test module 30, in which the gas-measuring device 40 is inserted. As can be recognized in FIG. 2f, the second feed valve 35 is again closed for this and the first feed valve 34 is opened. The selected test gas P1 can subsequently flow into the test module 30 and further into the gas-measuring device 40. The gas-measuring device 40 then outputs a second measured value m2, which is passed on via the data exchange means 31 to the control and analysis unit 21. A second measured value m2 of the gas sensor of the gas-measuring device 40 is thus detected according to step l. The control and analysis unit 21 thereupon determines, according to step m., based on the first measured value m1 detected and the second measured value m2 determined, whether a sensor poisoning is present. It is recognized in FIG. 2f that the control and analysis unit 21 displays information on the result determined by means of the output unit 27.

Figure 3A:
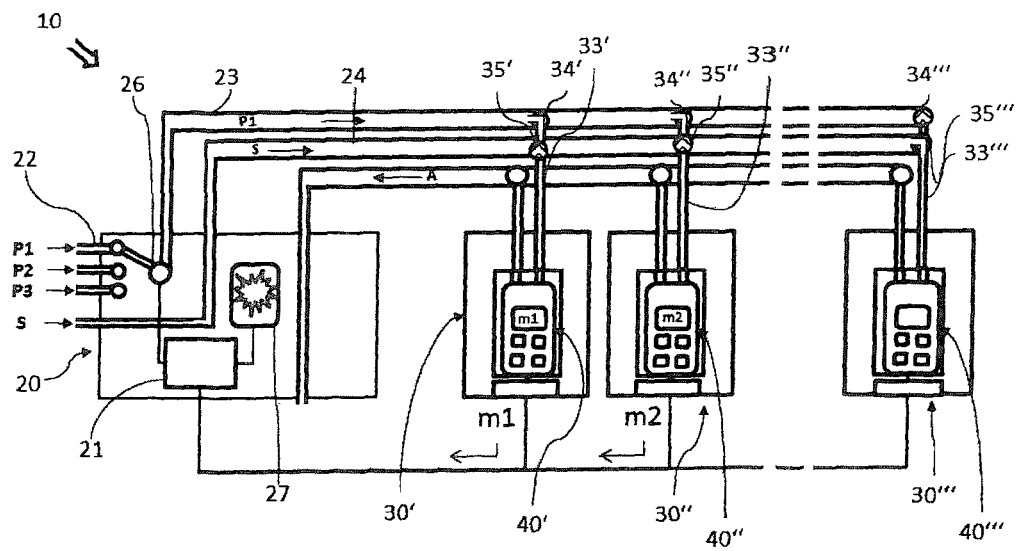
FIG. 3a is a detail showing a state during the course of the method in case of a plurality of gas-measuring devices inserted independently from one another into the test station.

Gas-measuring devices 40', 40", 40"', which were inserted into the test station 10 at different times, are located in a plurality of test modules 30', 30", 30"' in FIG. 3a. The gas-measuring devices 40' and 40" inserted into the test modules 30' and 30" are exposed to the test gas P1 at the time indicated in FIG. 3a. The first feed valves 34' and 34" belonging to the test modules 30' and 30" are opened, while the second feed valves 35' and 35" are closed. The test gas P1 is not selected either as the first test gas or as the second test gas for the gas-measuring device 40"' inserted into the test module 30"'. The feed valve 34"' is therefore closed at the time shown in FIG. 3a and the second feed valve 35"' is opened. It is recognized, furthermore, in FIG. 3a that the test gas P1 is used for the gas-measuring device 40' to determine the first measured value m1 for this gas-measuring device 40'. By contrast, the test gas P1 is used for the gas-measuring device 40" to determine already the second measured value m2 for this gas-measuring device 40'. The control and analysis unit 21 can therefore already determine for the gas-measuring device 40" according to step m. whether sensor poisoning is present and it sends information about this by means of the analysis unit 27. FIG. 3a, therefore, shows the test station 10 at a time at which steps a. through d. and i. have been carried out independently from one another corresponding to step A of the above-described method for each of the gas-measuring devices 40', 40", 40"' and at which it is determined, corresponding to step B of the above-described method, by means of the control and analysis unit 21 that the test modules 30', 30", 30"' are equipped with gas-measuring devices 40', 40", 40"'. Furthermore, it is already determined at the time shown in FIG. 3a according to step B which of the gas-measuring devices 40', 40", 40"' need the same test gas P1 as the next gas. These are the gas-measuring devices 40' and 40" in the case being shown. The gas-measuring device 40' needs this test gas P1 for carrying out step g. and the gas-measuring device 40" needs this test gas P1 for carrying out step l.

The gas-measuring device 40' will consequently have run through steps a. through g. at the time shown in FIG. 3a, the gas-measuring device 40' will have run through steps a. through d. and the method is concluded for the gas-measuring device 40" after step m. has been carried out.

Figure 3B:
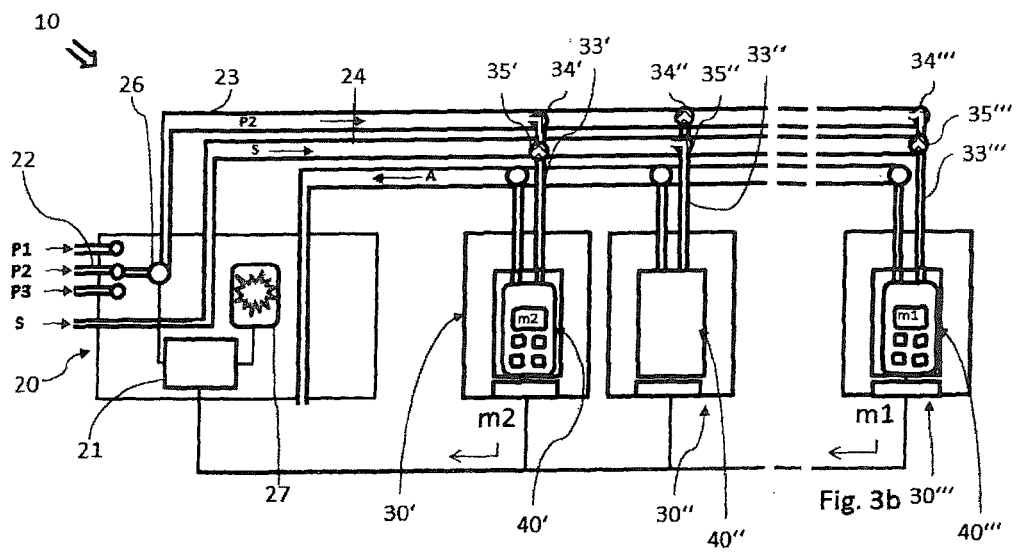
FIG. 3b is a detail showing another state during the course of the method in case of a plurality of gas-measuring devices inserted independently from one another into the test station.

Accordingly, as is recognized in FIG. 3b, the gas-measuring device 40" is removed from the test module 30" at the next point in time. Therefore, gas-measuring devices 40', 40' are inserted into the test modules 30' and 30' only at the time shown in FIG. 3b. Corresponding to step B of the above-described method, this is already determined by the control and analysis unit 21. The feed valve 34''' is consequently closed already corresponding to step C of the above-described method. Furthermore, it is likewise determined corresponding to step B of the above-described method that the gas-measuring devices 40' and 40' inserted into the test modules 30' and 30''' already need both the test gas P2 as the next test gas P1, P2, P3. The gas inlet 22, through which the test gas P2 can be fed, is then connected to the first gas feed line 23. The feed valves 34' and 34''' are opened, and the feed valves 35' and 35' are closed. The test gas P2 therefore flows both into the gas-measuring device 40' and into the gas-measuring device 40'.

The second measured value m2 is detected in this case for the gas-measuring device 40' according to step l., and it is determined by the control and analysis unit 21 according to step m. whether sensor poisoning is present, and it is recognized that the control and analysis unit 21 indicates the result of step m. by means of the output unit 27.

At the same time, the first measured value m1 is detected according to step g. for the gas-measuring device 40'''.

The method is therefore concluded after carrying out step m. for the gas-measuring device 40' at the time shown in FIG. 3b. The gas-measuring device 40''' will have run through steps a. through g. at this point in time.

Figure 3C:
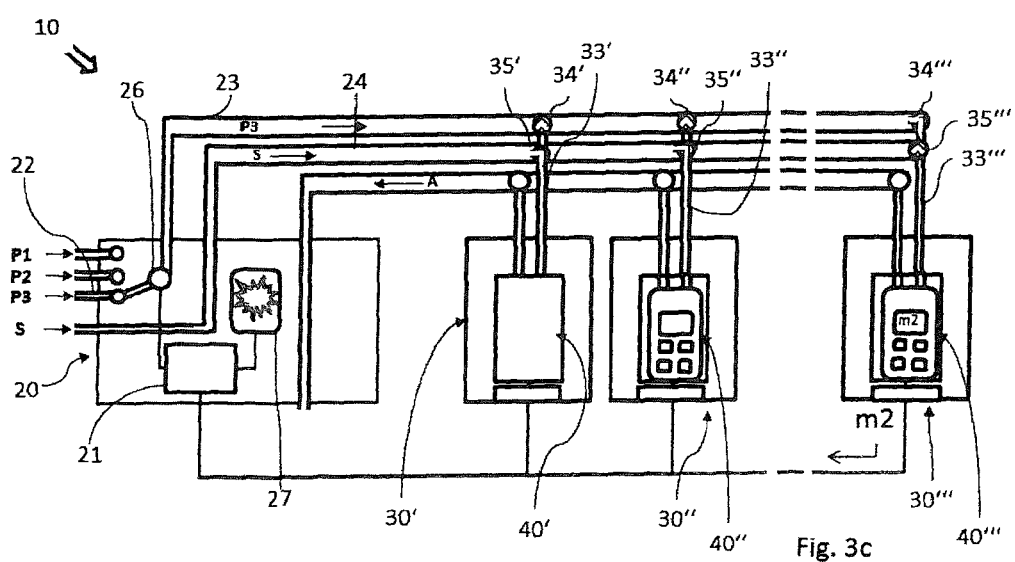
FIG. 3c is a detail showing another state during the course of the method in case of a plurality of gas-measuring devices inserted independently from one another into the test station.

The gas-measuring device 40' is then removed from the test module 30' at the time shown in FIG. 3c. The next gas-measuring device 40'''' may already be inserted into the test module 30''. Steps l. and m. are carried out for the gas-measuring device 40''' at this point in time. The first gas feed line 23 is connected in this case to the gas inlet 22, through which the test gas P3 can be fed. It is recognized that steps a. through m. are carried out at least once for all three gas-measuring devices 40', 40'', 40''' inserted into the test station 10 at the time shown in FIG. 3a, and the test station always carries out the following steps:

A. Carrying out steps a. and d. and/or carrying out step i. for each of the gas-measuring devices 40', 40'', 40''' independently from one another;

B. Determining, by means of the control and analysis unit 21, which of the test modules 30', 30'', 30''' are equipped with gas-measuring devices 40', 40'', 40''' and which of these gas-measuring devices 40', 40'', 40''' need the same test gas P1, P2, P3 as the next test gas;

C. Closing the feed valve 34', 34'', 34''', which is arranged between the first gas feed line 23 and the respective test module 30', 30'', 30''', for all test modules 30', 30'', 30''', which do not need the test gas P1, P2, P3 selected in B in the next step; and D. Carrying out steps e. through h. or steps j. through m. for each of the gas-measuring devices 40', 40'', 40''' determined in B independently from one another.

The test gas P1, P2, P3 may be selected from among one of the following gas mixtures in all the above-described exemplary embodiments:

Propane;
Propane mixed with $H_2S$, CO, $O_2$ and/or $CO_2$;
Pentane;
Pentane mixed with $H_2S$, CO, $O_2$ and/or $CO_2$;
Butane;
Hydrogen;
Methane;
Methane mixed with $H_2S$, CO, $O_2$ and/or $CO_2$; and
Mixtures of these gas mixtures mentioned.

For example:
test gas P1 may be (2.5 vol. % $CH_4$);
test gas P2 may be (0.9 vol. % $C_4H_{10}$); and
test gas P3 may be (mixed gas containing 0.4 vol. % $C_3H_8$, 18 vol. % $O_2$, 2 vol. % $CO_2$, 50 ppm CO, 15 ppm $H_2S$ in $N_2$)

in the example described in FIGS. 2a through 2f as well as in the example described in FIGS. 3a through 3c.

Other test gases and other concentrations are, of course, conceivable.

All the features and advantages emerging from the description, claims and drawings, including design details, arrangements in space and method steps may be essential for the present invention both alone and in the different combinations. While specific embodiments of the invention have been shown and described in detail to illustrate the application of the principles of the invention, it will be understood that the invention may be embodied otherwise without departing from such principles.

| APPENDIX | |
|---|---|
| A | Gas |
| P1 | Test gas |
| P2 | Test gas |
| P3 | Test gas |
| S | Purging gas |
| 10 | Test station |
| 20 | Main unit |
| 21 | Control and analysis unit |
| 22 | Gas inlet |
| 23 | Gas feed line |
| 24 | Gas feed line |
| 25 | Gas feed line |
| 26 | Port |
| 27 | Output unit |
| 28 | Data exchange means |
| 30 | Test module |
| 31 | Data exchange means |
| 32 | Mount |
| 33 | Gas feed line |
| 34 | Feed valve |
| 35 | Feed valve |
| 36 | Gas drain line |
| 37 | Port |
| 40 | Gas-measuring device |
| 41 | Gas inlet |
| 42 | Gas outlet |
| 50 | Device model recognition means |

What is claimed is:

1. A method for recognizing sensor poisonings of one or more portable gas-measuring devices, the method comprising the steps of:

providing a test station comprising a main unit including a control and analysis unit, a plurality of test modules connected with the main unit, each of the test modules for operative connection with one of the portable gas-measuring devices for data exchange, wherein the test station has device model recognition means for detecting at least one of a device model and gas sensor model of the gas sensor of the gas-measuring device operatively connected to a respective test module, wherein the main unit has a plurality of gas inlets, each of the inlets for one of different test gases, and wherein the test station has a first gas feed line, through which test gas is sent to the test modules, a second gas feed line, through which a purging gas is sent to the test modules, and a gas drain line, through which gas can be sent back to the main unit from the test modules;

connecting at least one gas-measuring device to one of the test modules of the test station;

recognizing at least one of the model of the gas sensor of the gas-measuring device connected and the device model of the gas-measuring device connected by the device model recognition means of the test station;

transmitting, the recognized at least one of the gas sensor model and the device model of the gas-measuring device connected, to the control and analysis unit;

selecting a first test gas, suitable for the gas sensor model of the gas-measuring device connected, by the control and analysis unit;

connecting a gas inlet, of the plurality of gas inlets, through which the selected test gas can be fed, to the first gas feed line;

feeding the first test gas to the test module, to which the gas-measuring device is connected;

detecting a first measured value of the gas sensor of the gas-measuring device;

one of purging and not purging the gas-measuring device and the gas sensor by means of a purging gas, which is sent through the second gas feed line from the main unit to the test module, into which the gas-measuring device is connected;

selecting a second test gas suitable for the gas sensor model of the gas-measuring device connected by the control and analysis unit;

connecting the gas inlet, of the plurality of gas inlets, through which the selected second test gas can be fed, to the first gas feed line;

feeding the second test gas to the test module, to which the gas-measuring device is connected;

detecting a second measured value of the gas sensor of the gas-measuring device; and determining whether sensor poisoning is present on the basis of the first measured value detected and the second measured value detected, wherein the first test gas contains a gas that is to be measured during the operation of the gas-measuring device at a first, known concentration and the second test gas contains the gas to be measured at a second, known concentration, which is different from the concentration of the gas in the first test gas, wherein the step of determining whether sensor poisoning is present further comprises the steps of:

transmitting the first and second measured values to the control and analysis unit of the test station;

determining a ratio of the first measured value to the second measured value; and at least one of outputting the ratio by means of an output unit and selecting a follow-up action by the control and analysis unit of the test station on the basis of the ratio determined.

2. A method in accordance with claim 1, wherein the second test gas contains, in addition to the gas to be measured, at least one gas for which the gas sensor model of the gas-measuring device connected has cross sensitivity.

3. A method in accordance with claim 2, wherein the gas to which there is cross sensitivity is not a component of the first test gas.

4. A method in accordance with claim 1, wherein each of the test modules, of the test station provided, comprise a gas feed line, which can be connected with the gas-measuring device to be tested, which has a first feed valve and a second feed valve and which can be connected with the first gas feed line via the first feed valve and with the second gas feed line via the second feed valve, wherein the step of feeding of the first test gas to the test module and the step of feeding of the second test gas to the test module further each comprise the steps of:

closing of the second feed valve; and
opening of the first feed valve.

5. A method in accordance with claim 1, wherein a plurality of gas-measuring devices are connected into the test station at the same time.

6. A method in accordance with claim 5, further comprising the steps of:

for each of the gas-measuring devices, independently carrying out at least one of: the steps of connecting at least one gas-measuring device, recognizing at least one of the model of the gas sensor and the device model, transmitting, the recognized at least one of the model of the gas sensor and the device model and selecting a first test gas; and the step of detecting a second measured value;

determining, by means of the control and analysis unit, which of the test modules are equipped with gas-measuring devices and which of the gas-measuring devices need a same test gas as the next test gas;

closing of the feed valve, which is arranged between the first gas feed line and the respective test module, for all test modules that do not need the same test gas; and for each of the gas-measuring devices, independently carrying out at least one of: the steps of connecting a gas inlet, feeding the first test gas, detecting a first measured value and one of purging and not purging; and connecting the gas inlet, of the plurality of gas inlets, through which the selected second test gas can be fed, to the first gas feed line; and the steps of feeding the second test gas, detecting a second measured value and determining whether sensor poisoning is present, wherein each of the steps of connecting at least one gas-measuring device, recognizing at least one of the gas sensor model and the device model, transmitting, the recognized at least one of the gas sensor model and the device model, selecting a first test gas, connecting a gas inlet, feeding the first test gas, detecting a first measured value, one of purging and not purging, selecting a second test gas, connecting the gas inlet, feeding the second test gas, detecting a second measured value and determining whether sensor poisoning is present is carried out at least once for each gas-measuring device that is connected into a test module of the test station.

7. A test station for recognizing sensor poisonings of one or more portable gas-measuring devices, the test station comprising:

a main unit comprising a control and analysis unit, a plurality of gas inlets for different test gases, a plurality of test modules connected with the main unit for data exchange with the main module, each of the test modules having a feature for connecting one of the gas-measuring devices;

a device model recognition means for detecting at least one of a device model and a gas sensor model of connected gas-measuring devices;

a first gas feed line through which test gas is fed to the test modules;

a second gas feed line through which a purging gas is fed to the test modules; and a gas drain line through which gas can be sent back to the main unit from the test modules, wherein the control and analysis unit is configured for:

selecting a first test gas suitable for the gas sensor model of the gas-measuring device connected;

connecting a gas inlet, of the plurality of gas inlets, through which the selected test gas can be fed, to the first gas feed line;

feeding the first test gas to the test module, to which the gas-measuring device is connected;

detecting a first measured value of the gas sensor of the gas-measuring device;

one of purging and not purging the gas-measuring device and the gas sensor by means of a purging gas, which is sent through the second gas feed line from the main unit to the test module, into which the gas-measuring device is connected;

selecting a second test gas suitable for the gas sensor model of the gas-measuring device connected;

connecting the gas inlet, of the plurality of gas inlets, through which the selected second test gas can be fed, to the first gas feed line;

feeding the second test gas to the test module, to which the gas-measuring device is connected;

detecting a second measured value of the gas sensor of the gas-measuring device; and determining whether sensor poisoning is present on the basis of the first measured value detected and the second measured value detected, wherein the first test gas contains a gas that is to be measured during the operation of the gas-measuring device at a first, known concentration and the second test gas contains the gas to be measured at a second, known concentration, which is different from the concentration of the gas in the first test gas and wherein the recognized at least one of the gas sensor model and the device model of the gas-measuring device is transmitted to the control and analysis unit, wherein the determination of whether sensor poisoning is present by the control and analysis unit includes a comparison of a ratio of the measured values with an expected ratio for the two test gases.

8. A test station in accordance with claim 7, wherein the control and analysis unit is configured for:

carrying out, independently for each of the gas-measuring devices, at least one of: the steps of connecting at least one gas-measuring device, recognizing at least one of the model of the gas sensor and the device model, transmitting, the recognized at least one of the model of the gas sensor and the device model and selecting a first test gas; and the step of detecting a second measured value;

determining, by means of the control and analysis unit, which of the test modules are equipped with gas-measuring devices and which of the gas-measuring devices need a same test gas as the next test gas;

closing of the feed valve, which is arranged between the first gas feed line and the respective test module, for all test modules that do not need the same test gas; and carrying out, independently for each of the gas-measuring devices, at least one of: the steps of connecting a gas inlet, feeding the first test gas, detecting a first measured value and one of purging and not purging; and connecting the gas inlet, of the plurality of gas inlets, through which the selected second test gas can be fed, to the first gas feed line; and the steps of feeding the second test gas, detecting a second measured value and determining whether sensor poisoning is present, wherein each of the steps of connecting at least one gas-measuring device, recognizing at least one of the gas sensor model and the device model, transmitting, the recognized at least one of the gas sensor model and the device model, selecting a first test gas, connecting a gas inlet, feeding the first test gas, detecting a first measured value, one of purging and not purging, selecting a second test gas, connecting the gas inlet, feeding the second test gas, detecting a second measured value and determining whether sensor poisoning is present is carried out at least once for each gas-measuring device that is connected into a test module of the test station.

9. A test station in accordance with claim 8, wherein the gas feed line of each test module is connected fluidically with the gas inlet of a gas-measuring device to be tested when the gas-measuring device is connected into the test module.

10. A test station in accordance with claim 8, wherein each test module has a gas drain line, which is connectable with the gas drain line of the test station.

11. A test station in accordance with claim 7, wherein the gas feed line of each test module is connected fluidically with the gas inlet of a gas-measuring device to be tested when the gas-measuring device is connected into the test module.

12. A test station in accordance with claim 11, wherein each test module has a gas drain line, which is connectable with the gas drain line of the test station.

13. A test station in accordance with claim 7, wherein each test module has a gas drain line, which is connectable with the gas drain line of the test station.

14. A test station in accordance with claim 13, wherein the gas feed line of at least one test module has a first feed valve and a second feed valve, wherein the gas feed line of the at least one test module is connected with the first gas feed line via the first feed valve and is connected with the second gas feed line via the second feed valve.

15. A test station in accordance with claim 7, wherein each test module has a gas drain line, which is connectable with the gas drain line of the test station.

16. A method for recognizing sensor poisonings of one or more portable gas-measuring devices, the method comprising the steps of:

providing a test station comprising a main unit including a control and analysis unit, a plurality of test modules connected with the main unit, each of the test modules for operative connection with one of the portable gas-measuring devices for data exchange, wherein the test station has device model recognition means for detecting at least one of a device model and gas sensor model of the gas sensor of the gas-measuring device operatively connected to a respective test module, wherein the main unit has a plurality of gas inlets, each of the inlets for one of different test gases, and wherein the test station has a first gas feed line, through which test gas is sent to the test modules, a second gas feed line, through which a purging gas is sent to the test modules, and a gas drain line, through which gas can be sent back to the main unit from the test modules;

connecting at least one gas-measuring device to one of the test modules of the test station;

recognizing at least one of the model of the gas sensor of the gas-measuring device connected and the device model of the gas-measuring device connected by the device model recognition means of the test station;

transmitting, the recognized at least one of the gas sensor model and the device model of the gas-measuring device connected, to the control and analysis unit;

selecting a first test gas, suitable for the gas sensor model of the gas-measuring device connected, by the control and analysis unit;

connecting a gas inlet, of the plurality of gas inlets, through which the selected test gas can be fed, to the first gas feed line;

feeding the first test gas to the test module, to which the gas-measuring device is connected;

detecting a first measured value of the gas sensor of the gas-measuring device;

one of purging and not purging the gas-measuring device and the gas sensor by means of a purging gas, which is sent through the second gas feed line from the main unit to the test module, into which the gas-measuring device is connected;

selecting a second test gas suitable for the gas sensor model of the gas-measuring device connected by the control and analysis unit;

connecting the gas inlet, of the plurality of gas inlets, through which the selected second test gas can be fed, to the first gas feed line;

feeding the second test gas to the test module, to which the gas-measuring device is connected;

detecting a second measured value of the gas sensor of the gas-measuring device; and determining whether sensor poisoning is present on the basis of the first measured value detected and the second measured value detected, wherein the first test gas contains a gas that is to be measured during the operation of the gas-measuring device at a first, known concentration and the second test gas contains the gas to be measured at a second, known concentration, which is different from the concentration of the gas to be measured in the first test gas and the determination of whether sensor poisoning is present further comprises a comparison of a ratio of the measured values with an expected ratio for the two test gases.

17. A method in accordance with claim 16, wherein the step of determining whether sensor poisoning is present further comprises the steps of:
   transmitting the first and second measured values to the control and analysis unit of the test station;
   determining the ratio of the first measured value to the second measured value; and
   at least one of outputting the ratio by means of an output unit and selecting a follow-up action by the control and analysis unit of the test station on the basis of the ratio determined.

18. A method in accordance with claim 16, wherein the second test gas contains, in addition to the gas to be measured, at least one gas for which the gas sensor model of the gas-measuring device connected has cross sensitivity.

19. A method in accordance with claim 18, wherein the gas to which there is cross sensitivity is not a component of the first test gas.

20. A method in accordance with claim 16, wherein each of the test modules, of the test station provided, comprise a gas feed line, which can be connected with the gas-measuring device to be tested, which has a first feed valve and a second feed valve and which can be connected with the first gas feed line via the first feed valve and with the second gas feed line via the second feed valve, wherein the step of feeding of the first test gas to the test module and the step of feeding of the second test gas to the test module further each comprise the steps of:
   closing of the second feed valve; and
   opening of the first feed valve.

21. A method in accordance with claim 16, wherein a plurality of gas-measuring devices are connected into the test station at the same time.

22. A method in accordance with claim 21, further comprising the steps of:
   for each of the gas-measuring devices, independently carrying out at least one of: the steps of connecting at least one gas-measuring device, recognizing at least one of the model of the gas sensor and the device model, transmitting, the recognized at least one of the model of the gas sensor and the device model and selecting a first test gas; and the step of detecting a second measured value;
   determining, by means of the control and analysis unit, which of the test modules are equipped with gas-measuring devices and which of the gas-measuring devices need a same test gas as the next test gas;
   closing of the feed valve, which is arranged between the first gas feed line and the respective test module, for all test modules that do not need the same test gas; and
   for each of the gas-measuring devices, independently carrying out at least one of: the steps of connecting a gas inlet, feeding the first test gas, detecting a first measured value and one of purging and not purging; and connecting the gas inlet, of the plurality of gas inlets, through which the selected second test gas can be fed, to the first gas feed line; and the steps of feeding the second test gas, detecting a second measured value and determining whether sensor poisoning is present, wherein each of the steps of connecting at least one gas-measuring device, recognizing at least one of the gas sensor model and the device model, transmitting, the recognized at least one of the gas sensor model and the device model, selecting a first test gas, connecting a gas inlet, feeding the first test gas, detecting a first measured value, one of purging and not purging, selecting a second test gas, connecting the gas inlet, feeding the second test gas, detecting a second measured value and determining whether sensor poisoning is present is carried out at least once for each gas-measuring device that is connected into a test module of the test station.

* * * * *